US010623665B2

(12) United States Patent
Priest

(10) Patent No.: US 10,623,665 B2
(45) Date of Patent: *Apr. 14, 2020

(54) CONVERTER DEVICE AND SYSTEM INCLUDING CONVERTER DEVICE

(71) Applicant: BLACK DIAMOND VIDEO, INC., Richmond, CA (US)

(72) Inventor: Edward Priest, Point Richmond, CA (US)

(73) Assignee: BLACK DIAMOND VIDEO, INC., Richmond, CA (US)

( * ) Notice: Subject to any disclaimer, the term of this patent is extended or adjusted under 35 U.S.C. 154(b) by 49 days.

This patent is subject to a terminal disclaimer.

(21) Appl. No.: 15/269,971

(22) Filed: Sep. 19, 2016

(65) Prior Publication Data

US 2017/0013204 A1    Jan. 12, 2017

Related U.S. Application Data

(63) Continuation of application No. 14/637,332, filed on Mar. 3, 2015, now Pat. No. 9,544,533.

(Continued)

(51) Int. Cl.
*H04N 5/268*    (2006.01)
*H04N 7/01*    (2006.01)
(Continued)

(52) U.S. Cl.
CPC .......... *H04N 5/268* (2013.01); *A61B 1/0005* (2013.01); *A61B 1/041* (2013.01); *A61B 5/0035* (2013.01);
(Continued)

(58) Field of Classification Search
CPC .......... H04N 7/01; H04N 5/268; H04N 5/265; G06F 19/321; G06F 19/3418; G06F 19/3481; A61B 1/041
(Continued)

(56) References Cited

U.S. PATENT DOCUMENTS 4,888,795 A * 12/1989 Ando ................. H04N 1/33307
  348/14.14
4,910,609 A *  3/1990 Nicholas ................ H04N 19/60
  358/426.01

(Continued)

OTHER PUBLICATIONS

PCT/US2015/018546. Applicant: Black Diamond Video. Int'l Search Report & Written Opinion (dated Sep. 21, 2015).

*Primary Examiner* — Michael E Teitelbaum
*Assistant Examiner* — Sean N. Haiem
(74) *Attorney, Agent, or Firm* — Loza & Loza, LLP; Michael I. Angert

(57) ABSTRACT

Systems and apparatus may include converter device(s), a matrix switch, processor(s), and memory(s), where one or more of the converter devices provide video input signals to the matrix switch. A processor may determine if one of a plurality of video signals input to the matrix switch includes data representative of identification information overlain on a video image derived from one of the plurality of video signals. The determination may be based on a flag value stored in the converter device(s). The flag value may be retrieved by a server coupled to the matrix switch. If the information is included in the video signal, the video signal may be passed through a path in a matrix switch configured by the processor. If the information is not included in the video signal, the data representative of identification information may be retrieved from the converter device and then overlain on the video image.

20 Claims, 8 Drawing Sheets

Related U.S. Application Data

(60) Provisional application No. 61/947,934, filed on Mar. 4, 2014.

(51) Int. Cl.
  *G06F 19/00* (2018.01)
  *A61B 1/00* (2006.01)
  *A61B 5/00* (2006.01)
  *A61B 1/04* (2006.01)
  *H04N 5/265* (2006.01)
  *A61B 8/00* (2006.01)

(52) U.S. Cl.
  CPC .......... *G06F 19/321* (2013.01); *G06F 19/328* (2013.01); *G06F 19/3418* (2013.01); *G06F 19/3481* (2013.01); *H04N 5/265* (2013.01); *H04N 7/01* (2013.01); *A61B 8/00* (2013.01)

(58) Field of Classification Search
  USPC ............ 348/441, 14.04, 45; 705/3; 715/804; 340/635; 248/124.1; 345/629; 725/68
  See application file for complete search history.

(56) References Cited

U.S. PATENT DOCUMENTS

| | | | | |
|---|---|---|---|---|
| 6,437,834 B1* | 8/2002 | Tagami | .................. | H04N 5/265 348/554 |
| 6,621,526 B1* | 9/2003 | Yamagishi | ............. | H04N 9/641 345/604 |
| 7,920,557 B2* | 4/2011 | Moote | ..................... | H04L 45/60 370/389 |
| 7,975,085 B2* | 7/2011 | Hattori | ................ | G06F 13/4059 710/10 |
| 2001/0024240 A1* | 9/2001 | Fujita | ..................... | H04N 5/268 348/705 |
| 2007/0143576 A1* | 6/2007 | Ellgen | .................... | H04N 5/268 712/10 |
| 2007/0273759 A1* | 11/2007 | Krupnick | ............... | H04N 5/225 348/45 |
| 2009/0173846 A1* | 7/2009 | Katz | ...................... | A61B 90/50 248/124.1 |
| 2010/0295870 A1* | 11/2010 | Baghdadi | ............... | G09G 5/005 345/650 |
| 2011/0074591 A1* | 3/2011 | Arling | ................. | H04N 21/4126 340/635 |
| 2011/0077965 A1* | 3/2011 | Nolte | .................... | G06Q 10/10 705/3 |
| 2011/0267418 A1* | 11/2011 | Galindo | ................... | H04N 7/15 348/14.04 |
| 2012/0278759 A1* | 11/2012 | Curl | ...................... | G06F 19/327 715/804 |
| 2013/0201316 A1* | 8/2013 | Binder | .................... | H04L 67/12 348/77 |
| 2013/0300829 A1* | 11/2013 | Urasaki | ............. | A61B 1/00009 348/45 |
| 2013/0317837 A1* | 11/2013 | Ballantyne | .......... | A61M 1/1037 705/2 |
| 2014/0033258 A1* | 1/2014 | Beals | ..................... | H04H 20/63 725/68 |
| 2014/0165081 A1* | 6/2014 | Jeffery | ................. | H04L 1/0003 725/1 |
| 2014/0348183 A1* | 11/2014 | Kim | ..................... | H04L 7/0041 370/503 |
| 2015/0154778 A1* | 6/2015 | Hughes | ................. | G06F 19/321 345/629 |

\* cited by examiner

CONVERTER DEVICE AND SYSTEM INCLUDING CONVERTER DEVICE

CROSS-REFERENCE TO RELATED APPLICATIONS

The present application for patent is a continuation application of U.S. patent application Ser. No. 14/637,332 entitled "Converter Device and System Including Converter Device" filed Mar. 3, 2015, which in turn claims priority to U.S. provisional application No. 61/947,934 entitled "Smart Converter Apparatus and Communication System" filed Mar. 4, 2014, the entire disclosures of which are hereby expressly incorporated by reference.

BACKGROUND

Field

Various features relate to interface devices for video and audio, and in particular, to interface devices adapted to receive data in any one of a plurality of format types, convert the data to one predetermined format type, add metadata, and output the converted data including the metadata for analysis and/or storage.

Background

Today's surgical operating rooms contain a myriad of technology. The technology includes equipment that provides video as an output. As used herein, the term video is meant to encompass, for example, moving images of live action (e.g., images of an interior of a patient's body as a laparoscope is maneuvered therein, of an interior of a large intestine as an endoscope is advanced through the intestine, or of an operating room as operating room staff move about therein), still images (e.g., individual frames captured from a moving image of live action), real-time or near real time images that have been generated with the aid of a computing device (e.g., images of an interior of a patient's body generated by a sonogram machine, a magnetic resonance imaging (MRI) machine, or an X-ray machine), as well as graphic representations of static, semi-static, and dynamic measurements of parameters (e.g., an image from a screen of an electrocardiograph machine, a display of bold oxygen concentration, or blood pressure). The preceding list is demonstrative and is not intended to be limiting. Reference to video is also intended to encompass the signals presented to video monitors (e.g., monitors, televisions, cathode ray tubes (CRTs), liquid crystal displays (LCDs)) that drive the circuitry of video monitors to generate imagery. Some pieces of equipment may add some aspect of patient identification to their images and this information may typically be provided outside of the boundary edges of the images.

The video may be provided to video monitors integrated with the equipment (e.g., a video monitor integrated with a sonogram machine) and/or to video monitors within the operating room, and/or to video monitors outside of the operating room. The video may also be recorded at the time of its production, either by a recording device integrated with the equipment or by an external recording device coupled to the equipment.

Video may be obtained, for example, from video pickup devices (and circuitry associated therewith) or video output ports of medical devices such as endoscopes, laparoscopes, orthoscopes, microscopes, robotic surgical systems, surgical-light mounted video cameras, and video cameras mounted in the operating room that provide images of the operating room itself. Additional video may be obtained, for example, in the form of graphic displays of vital signs, such as those associated with electrocardiograph devices, bold oxygen monitoring device, and blood pressure monitoring device. Still further, video imagery may be obtained from fluoroscopes, X-ray machines (commonly referred to as "CR machines"), magnetic resonance image (MRI) machines, computed axial tomography (CAT) scanners, and/or other types of imaging devices. The preceding lists are demonstrative and are not intended to be limiting.

Instruments, machines, and/or devices found in today's operating rooms are made by many manufacturers. Each manufacturer may have a different preference for how its video signals are presented to video monitors (e.g., component video, red-green-blue (RGB) video, separate or super video (S-Video), digital signals) and what formats are used (e.g., analog NTSC or PAL or digital High Definition Multimedia Interface (HDMI), among others). Additionally, video signals may be provided from the equipment to the video monitors wirelessly, via copper wire, or via fiber optic cable. As used herein, a video output of any given piece of equipment may be referred to as a video feed.

There presently exists system that provides digital, video routing and display solutions to such environments as, for example, operating rooms, hybrid rooms, catheterization suites, interventional suites, and electrophysiology (EP) labs. The system may be configured with videoconferencing and streaming, multiview windowing, image capturing, video recording, and/or hands-free voice over Internet Protocol (IP) communication. The system may provide a user with comprehensive control over the system and its functionality, including, for example, touch routing of images from video and data sources to video monitor monitors.

The system may be useful, for example, for display of the video imagery of one or more pieces of equipment on one or more video monitors that are not integral to the equipment itself. Such video monitors may be conveniently positioned for a surgeon's use during surgery. The system may also be useful, for example, for remote (i.e., in a location other than the operating room) observation, training, and conferencing. The components of the system may be dispersed to multiple locations; some components may be in the operating room while other components may be outside of the operating room. The components of the system may be coupled to one another via wire, fiber optic cable, and/or via radio waves (i.e., wireless).

While the system is useful, several problems exist. For example, it is possible that the video from a given piece of equipment may not be displayed on a video monitor, despite the system having been programmed to route the video from the given piece of equipment to the video monitor. It may not be possible for operating room staff (or hospital staff in general) to determine if the lack of a video image is due to a failure of the given piece of equipment, a failure of the system or one of its components, or a failure of any of the wired, wireless, and/or fiber optic interconnections between the given piece of equipment, a server of the system, and the video monitor. Trouble-shooting such a problem can be time consuming and is, in general, not something that operating room staff (or hospital staff in general) are trained or equipped for.

Additionally, while the system may help in locating various pieces of equipment within the hospital setting, it is not able to provide information about the equipment with a degree of granularity that would be helpful, for example, in distinguishing between features of two pieces of equipment that share a same general name, such as "microscope."

Additionally, the system cannot apply such granular information (i.e., equipment information), and/or patient information, to video images presented on video monitors. Nor is the system able to remove patient information (or not display patient information if it is already present in a video stream) from a video monitor in a public area, such as at a conference, so as to comply with the Health Insurance Portability & Accountability Act of 1996 (HIPPA) regulations.

What is needed is a system, device, and/or method that solves one or more of these and/or other problems which may be recognized in the existing system.

SUMMARY

A system including one or more computers can be configured to perform particular operations or actions by virtue of having software, firmware, hardware, or a combination of them installed on the system so that in operation they cause the system to perform the actions. One or more computer programs can be configured to perform particular operations or actions by virtue of including instructions that, when executed by data processing apparatus, cause apparatus of the system to perform the actions.

In one general aspect, an apparatus may include a video converter, a processing circuit communicatively coupled to the video converter, and a non-volatile memory circuit communicatively coupled to the processing circuit, the non-volatile memory circuit may be configured to store data associated with a medical device that is associated with the apparatus. The data may include elapsed operating time of the medical device, a maintenance due date of the medical device, a flag indicative of a presence of patient information in an output of the medical device, a flag indicative of a presence of modality information in an output of the medical device, input video status, asset tracker identification number or sequence of numbers and or letters, and/or one or more x-y coordinates for the location of patient information on a video image.

According to one aspect of the apparatus, the processing circuit may be configured to dynamically select an output signal of the apparatus. The output signal may be selected, for instance, from between data representative of a video signal received at an input of the apparatus and data representative of a pre-defined video pattern. According to one aspect, the selection of the output signal may be based on a determination of validity of the video signal at the input of the apparatus. An image generator may be further coupled to the processing circuit. According to one aspect, a switch may be coupled to the video converter and the image generator, where the processing circuit may be configured to switch an output of the switch between the video converter and the image generator. According to this aspect, the processing circuit automatically switches the output of the switch between the video converter and the image generator based on a determination of the validity of the video signal that is input to the apparatus.

Another general aspect may include a method of converting video data, operational at a converter device. The method may include transmitting a value indicative of whether predetermined information will be included in video data to be received from equipment coupled to the converter device and determining if the converter device is receiving valid video data from the equipment coupled to the converter device. If the converter device is receiving valid video data, the converter device may convert the received video data from a first format to a second predefined format and may transmit the converted video data in the second format to a digital video matrix. If the converter device is not receiving valid video data, the converter device may generate data representative of a predetermined image and may transmit the generated data to the digital video matrix.

Still another aspect includes a system. The system may include a matrix switch configured to receive a plurality of video signals from video sources, a processor communicatively coupled to the matrix switch, a first memory communicatively coupled to the processor, where the processor may be configured to execute instructions stored in the first memory, the instructions causing the processor to determine if one of the plurality of video signals includes data representative of identification information overlain on a video image derived from one of the plurality of video signals. The instructions may further cause the processor to pass the video signal through a path in a matrix switch configured by the processor and add data representative of identification information overlain on the video image derived from the one of the plurality of video signals if the one of the video signal does not include the data or pass the video signal through the path in the matrix switch configured by the processor if the video signal does include the data.

Another aspect includes still another system. The system may include a video converter, a video converter processor communicatively coupled to the video converter, a first memory communicatively coupled to the video converter processor, a system processor, and a second memory communicatively coupled to the system processor. The system may further include a matrix switch communicatively coupled to the system processor and the video converter, where an output of the video converter is communicatively coupled to one of a plurality of matrix switch inputs. Furthermore, the system processor may configure the matrix switch to communicatively couple the one of the plurality of matrix switch inputs to one of a plurality of matrix switch outputs. Additionally, the system processor may execute instructions stored in the second memory to cause the system processor to determine if the video converter is communicatively coupled to a video source that includes identification information overlain on a video image derived from a video signal received from the video source. If not, the processor may pass the video signal from the one of the plurality of matrix switch inputs to the one of the plurality of matrix switch outputs and add identification information to the video signal to appear as an overlay on the video image derived from the video signal. If so, the processor may pass the video signal from the one of the plurality of matrix switch inputs to the one of a plurality of matrix switch outputs.

Yet another aspect may provide a converter device including a processor and a memory, where the memory may store instructions that, when executed by the processor, cause the processor to transmit a value indicative of whether predetermined information will be included in video data to be received from equipment coupled to the converter device and determine if the converter device is receiving valid video data from the equipment coupled to the converter device. According to this aspect, if the converter device is receiving valid video data then the processor may execute instructions to convert the received video data from a first format to a second predefined format, and may then transmit the converted video data in the second format to a digital video matrix. Still according to this aspect, if the converter device is not receiving valid video data then the processor may execute instructions to generate data representative of a predetermined image and transmit the generated data to the digital video matrix.

Still yet another aspect may provide for a system that includes a server. According to this aspect, the server may include a server processor, a server memory, communicatively coupled to the server processor, a matrix switch communicatively coupled to the server processor, a first plurality of matrix switch input ports communicatively coupled to the matrix switch, a second plurality of matrix switch output ports communicatively coupled to the matrix switch, the matrix switch input ports multiplexed to the matrix switch output ports under control of the server processor. According to this aspect, the system may also include a converter apparatus. The converter apparatus may have an input configured to receive a video signal from a video source and an output communicatively coupled to one of the first plurality of matrix switch input ports. The converter apparatus may further include a video converter configured to convert the video signal received from the video source from a first format into a second format, and transmit the converted video signal to the one of the first plurality of matrix switch input ports, a processing circuit communicatively coupled to the video converter, a non-volatile memory circuit communicatively coupled to the processing circuit, the non-volatile memory circuit configured to store data associated with the video source, the data may include at least one flag indicative of a presence of identification information in the video signal from the video source. According to this aspect, the server processor may execute commands stored in the server memory to retrieve a value of the at least one flag stored in the non-volatile memory of the converter apparatus, pass the video signal from the one of the first plurality of matrix switch input ports to one of the second plurality of matrix switch outputs and add identification information to the video signal to appear as an overlay on a video image derived from the video signal if the value of the at least one flag indicates identification information is not present. Alternatively, the server processor may execute commands stored in the server memory to pass the video signal from the one of the first plurality of matrix switch inputs to the one of the second plurality of matrix switch outputs if the at least one flag indicates identification information is present. The system according to this aspect may further include a first communication interface communicatively coupled to the server processor, and a second communication interface communicatively coupled to the processing circuit and the first communication interface. According to this aspect the server processor may retrieve the value of the at least one flag stored in the non-volatile memory of the converter apparatus via messaging between the first communication interface and the second communication interface. According to one feature, the server memory may be located remote to the non-volatile memory circuit. According to another feature, the video converter, processing circuit, and non-volatile memory may be logically and/or physically coupled to the video source.

The above described aspects and features may include computer systems, apparatus, and computer programs recorded on one or more computer storage devices, each configured to perform the actions of any of the methods described above.

DETAILED DESCRIPTION

Figure 1:
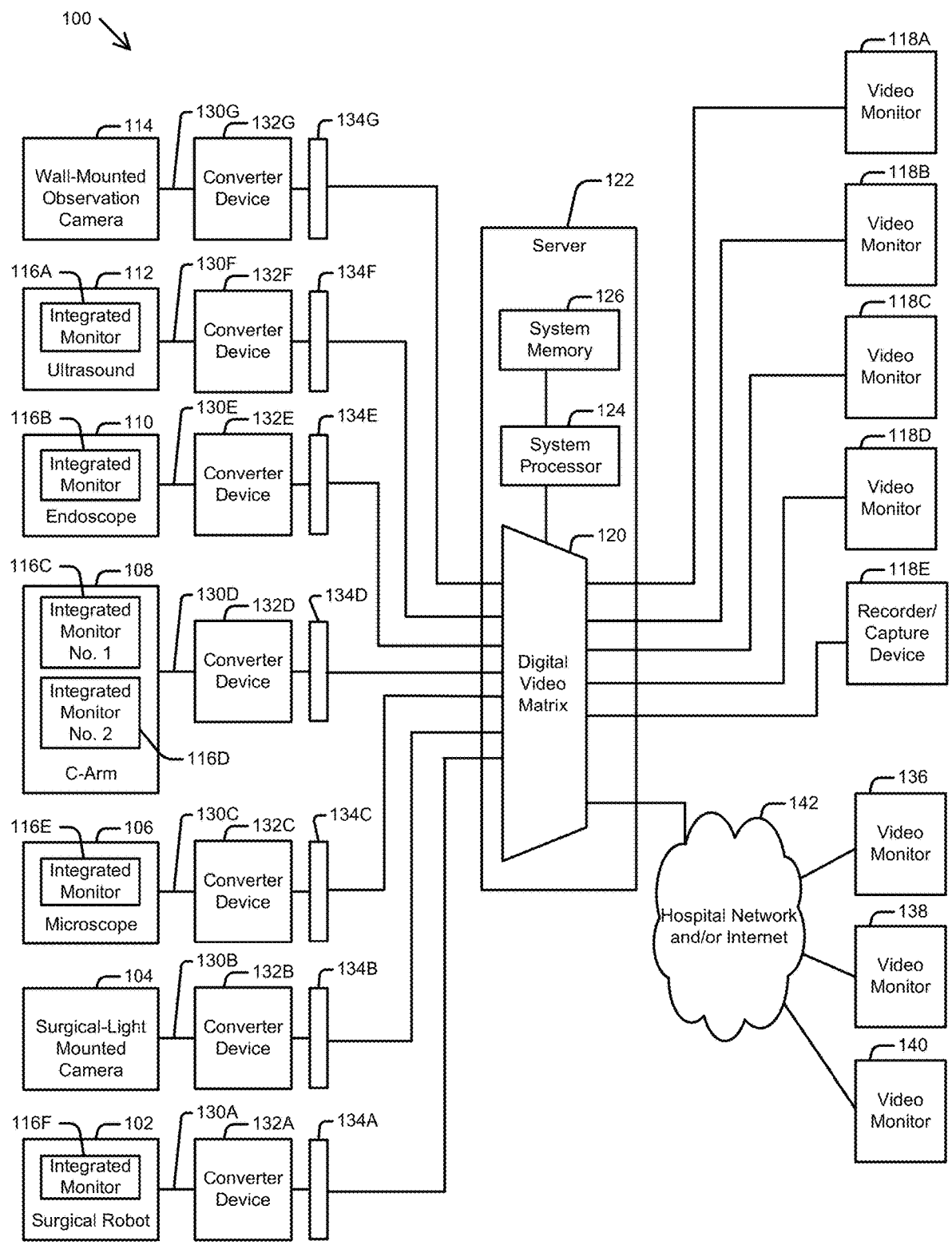
FIG. 1 provides an example of an operational environment 100 in which a system, including a converter device, may find utility.

In the following description numerous specific details may be set forth in order to provide a thorough understanding of the invention. However, one skilled in the art would recognize that the invention might be practiced without these specific details. In other instances, well known methods, procedures, and/or components have not been described in detail so as not to unnecessarily obscure aspects of the invention.

Overview

Described herein are one or more components of a system, including a matrix switch, that provides for the routing of multiple input video signals to one or more of a plurality of output video signals. The format of the video signals may be a high speed digital video interface such as Digital Video Interface (DVI) or some other digital video interface. DVI is a video monitor interface developed by the Digital Display Working Group (DDWG). DVI is useful for coupling a video source, such as a camera, to a video monitor. The video signals input to the matrix switch may come from cameras or other devices that provide output in the form of a video image. The video signal output from the matrix switch may be used to drive video monitors and/or input to recorder, image capture, streaming and/or conferencing devices.

The components of the system, either alone or in concert with the system as a whole, may permit a user to determine a source of a lack of video imagery on an otherwise functioning video monitor. The components of the system may also allow a user to distinguish between the capabilities of two pieces of equipment that each performs the same general function. Components of the system may also facilitate the presentation of, or prevent the presentation of, text overlays (or equivalents thereof) of patient information on video monitors, thereby improving safety and to protecting privacy.

According to one aspect, a component of the system may receive, from a given piece of equipment associated with that component, a video signal of a first type and convert the video signal to a second predetermined type for application to a digital video matrix. According to one aspect, the component may store data for identifying the given piece of equipment with greater granularity than previously existed. The component may store data indicative of whether the given piece of equipment associated with that component provides equipment information in a video stream presented to the component (e.g., a "modality provided by source" flag) and/or provides patient information in the video stream presented to the component (e.g., a "patient information provided by source" flag). The component may additionally or alternatively store data indicative of a status of a video signal input to the component, and may be configured to present predetermined video imagery on a monitor to indicate a failure to receive an expected video signal from the equipment to which it is associated. The component may be referred to as a converter device herein.

Operational Environment

FIG. 1 provides an example of an operational environment 100 in which a system, including a converter device, may find utility. The operational environment used to illustrate aspects of the system in general and the converter device in particular is that of a hospital and hospital operating rooms. This operational environment is for illustrative and descriptive purposes; it is not intended to be limiting.

An operating room may include, for example, a surgical robot 102, a surgical-light mounted camera 104, a microscope 106, a C-Arm 108 (mounting, for example, an X-ray or fluoroscope machine), an endoscope 110, an ultrasound machine 112, and an observation camera 114 mounted to a wall of the operating room.

As illustrated for exemplary purposes, the surgical-light mounted camera 104 and the observation camera 114 are shown without integrated video monitors. The surgical robot 102, microscope 106, endoscope cart 110, and ultrasound 112 are each depicted as having one integrated video monitor 116A, 116B, 116E, 116F. The C-arm 108 is depicted as having two integrated video monitors 116C, 116D. In addition, the operating room 100 may include one or more auxiliary video monitors 118A, 118B, 118C, 118D, and one or more recorders, image capture, streaming, and/or conferencing devices 118E that are coupled to a digital video matrix 120 coupled to a server 122 of the overall system.

The server 122 may include a processor of the overall system (referred to herein as a system processor 124) coupled to the digital video matrix 120 and a memory (referred to herein as a system memory 126) coupled to the system processor 124. The digital video matrix 120 and/or server 122 may be located inside or outside of the operating room.

In this description, there is a distinction drawn between the integrated video monitors 116A, 116B, 116C, 116D, 116E, 116F, which are understood to be the video monitors integral to their respective pieces of equipment 102, 106, 108, 110, 112—and the auxiliary video monitors 118A, 118B, 118C, 118D (hereinafter referred to as video monitors 118A, 118B, 118C, 118D or video monitors A-D) that are coupled to the digital video matrix 120 and which receive input from the digital video matrix 120. Any reference to a video monitor made hereinafter should be construed as a reference to an auxiliary video monitor such as video monitors 118A, 118B, 118C, 118D.

Each piece of equipment 102-114 may include a capability to provide, as an output, a video signal (referred to herein alternatively as a video feed or a video signal 130A, 130B, 130C, 130D, 130E, 130F, 130G) to generate an image on one or more video monitors 118A, 118B, 118C, 118D.

In the illustrative example of FIG. 1, the number of pieces of equipment 102-114 is greater than the number of video monitors 118A, 118B, 118C, 118D and/or recorders, image capture, streaming, and/or conferencing devices 118E. The example is not limiting; the number of pieces of equipment can be greater than, less than, or equal to the number of video monitors.

The system to multiplex a video feed from each of the pieces of equipment 102-114 to one or more video monitors (e.g., 118A-D) and/or recorders, image capture, streaming, and/or conferencing devices (e.g. 118E) may include a plurality of converter devices 132A, 132B, 132C, 132D, 132E, 132F, 132G (individually and collectively referred to as converter device(s) 132, converter devices 132A, 132B, 132C, 132D, 132E, 132F, or 132G, or converter devices 132A-G). One or more converter devices 132 may be associated with each piece of equipment 102-114. By way of example, in FIG. 1, there is a one-to-one relationship between a number of pieces of equipment 102, 104, 106, 108, 110, 112, 114 and the number of converter devices 132A, 132B, 132C, 132D, 132E, 132F, 132G, respectively.

According to one aspect, each converter device 132A-G may be configured to accept, as input, one video feed of a first type, convert the first type to a second predetermined type, and provide, as output, one video feed of the second type. The first and second types may be the same or different. Nothing herein is meant to limit the number of inputs and/or outputs of the converter devices 132A-G.

Each converter device 132 in the plurality of converter devices may be coupled to the digital video matrix 120. Coupling may be via an interface device 134A, 134B, 134C, 134D, 134E, 134F, 134G (individually and collectively referred to as interface device(s) 134).

In some aspects, voltage to operate the converter device 132 may be provided to the converter device 132 via the interface 134. In some aspects, voltage to operate the converter device 132 may be provided to the converter device 132 from an AC-DC converter (not shown). In some aspects, voltage to operate the converter device 132 may be provided to the converter device 132 from the piece of equipment to which the converter device is coupled.

As depicted in FIG. 1, the digital video matrix 120 may be coupled to video monitors 118A, 118B, 118C, 118D, and recorders, image capture, streaming, and/or conferencing devices 118E in the operating room. This list is exemplary and non-limiting. In one aspect, the video monitors may include, for example, a touch panel video monitor, an anesthesiologist's video monitor, a surgeon's video monitor, and a wall mounted video monitor. A fewer or greater number of video monitors are within the scope of any aspect described herein.

The digital video matrix 120 may also be coupled to remote video monitors, such as conference room video monitor 136, a nurses' station video monitor 138, and/or video monitors of administrative staff, such as, for example, a clinical engineering department video monitor 140. The clinical engineering department may have responsibility for inventory control and/or maintenance of the equipment to which the converter devices are attached. The digital video matrix 120 may also be coupled to mobile devices such as an iPad, iPhone, Android, etc. Coupling to remote monitors and mobile devices may be achieved at a home or office securely.

The coupling of the outputs of the plurality of converter devices 132 to the digital video matrix 120 and the coupling of the outputs from the digital video matrix 120 to remote video monitors 136, 138, 140, may be via the hospital's internal network 142. Using known communication and security protocols, any video monitor, including remote video monitors 136, 138, 140 may be coupled to the digital video matrix 120 via networks external to the hospital, such as the Internet.

System with Multiple Servers

Figure 2:
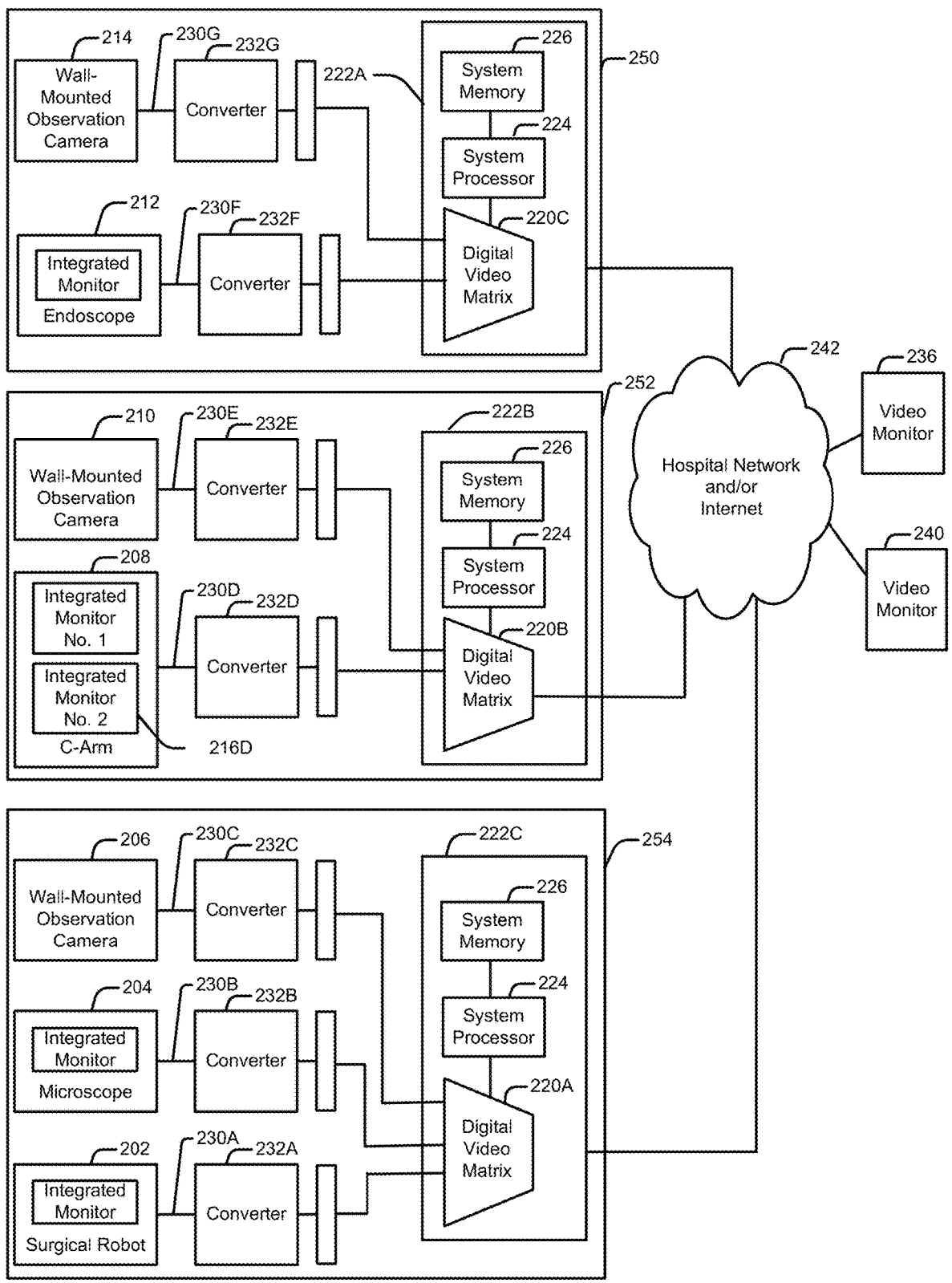
FIG. 2 is a block diagram illustrating an aspect in which three rooms, each served by their own server, send video out over a network.

FIG. 2 is a block diagram illustrating an aspect in which three rooms 250, 252, 254, each served by their own server 222A, 222B, 222C (similar to 122, FIG. 1), send video out over a network 242. The rooms may be operating rooms. Each server 222A, 222B, 222C may also send video to display devices and/or recording devices in the room in which it is located. Each server 222A, 222B, 222C may include its own digital video matrix 220A, 220B, 220C (similar to 120, FIG. 1).

In one aspect, a user at a remote video monitor, such as at a nurses' station video monitor 240 or a clinical engineering department video monitor 236, may be able to view a dynamically changing list of each piece of equipment 202, 204, 206, 208, 210, 212, 214 presently coupled to all servers 222A, 222B, 222C via converter devices 232A, 232B, 232C, 232D, 232E, 232F, 232G (similar to 132, FIG. 1). The list may include information at a level of granularity sufficient to distinguish between the features of two pieces of equipment that perform the same function.

For example if the hospital has three microscopes designated for use in operating rooms, there may be an assumption that each microscope is in its respective operating room and is being used throughout each scheduled surgery. In reality, a microscope, such as microscope 204 in operating room 254, might be used for a short period at the beginning, middle, or end of a surgical procedure. At other times, over the course of a surgery scheduled to last several hours, the valuable piece of equipment (i.e., the microscope 204) may be unused.

Use of the system, depicted in exemplary FIG. 2, permits a user at a remote video monitor (e.g., 236, 240) to visually observe each operating room 250, 252, 254 using a wall mounted camera 206, 210, 214 (each similar to 114, FIG. 1). While the illustrative example of FIG. 2 depicts a wall mounted camera in every room 250, 252, 254, no room is required to have a wall mounted camera. Their presence in FIG. 2 is for descriptive purposes. In one aspect, in addition to or instead of a wall mounted camera, a list of converter devices inside each operating room may be presented to a user in text and/or graphic form on a user's display. The list may show what is connected to the server and identify each piece of equipment using the parameters associated with the piece of equipment as previously programmed into the converter device. If a room camera is available it can be used to visually look into the operating room to see if the actual device is in use. If a given piece of equipment was used and unplugged, the list may show that it was previously connected to the router in the room but the text and/or graphics associated with the piece of equipment may be grayed out. Device tracking may also be supported. In this case, if a converter device and/or the piece of equipment to which it is coupled are equipped with an asset tracking device, then a system according to aspects described herein may obtain the asset tracking information through the hospital's network to locate the piece of equipment.

Returning to FIG. 2, observation, for example by wall mounted cameras 206, 210, 214 may permit one to determine whether the microscope 204 is in one of the operating rooms and, if in the operating room, may permit the user to determine if the microscope 204 is being used. The user may then identify, from the sufficiently high granularity of the information describing the microscope 204, whether the microscope 204 has a desired feature that other microscopes are lacking, for example, a certain type of optical filter. If the user can confirm that the microscope 204 has the desired feature, the user can ask an operating room 254 nurse if the microscope 204 can be removed from operating room 254. Removal may be due to a need to use the microscope in another operating room 250 or 252, for routine maintenance, or for warranty repair.

In one aspect, converter devices 232A-G, each coupled to a given piece of equipment 202-214, can be used to store multiple items of information about that particular piece of equipment that may be more useful than just a descriptor of the equipment type. In addition to equipment type, the stored information may include, for example, manufacturer, model number, serial number, total runtime (e.g., hours of operation), maintenance due date, asset tracker ID, and flags such as a flag to indicate whether the piece of equipment itself provides patient information in its video feed and/or a flag to indicate whether the piece of equipment itself provides modality information (e.g., manufacturer, model number, serial number, etc.) about itself in its video feed. The stored information can also include an indication of the status of the video 230A-G being received by the converter device 232 (e.g., video input present, or not present).

One or more of the exemplary types of information recited above may be entered into a memory device (e.g., 320, FIG. 3) of the converter device 232 and stored for future use. The information may be entered, for example, during setup of the converter device 232 when it is initially coupled to a given piece of equipment.

Converter Device

Figure 3:
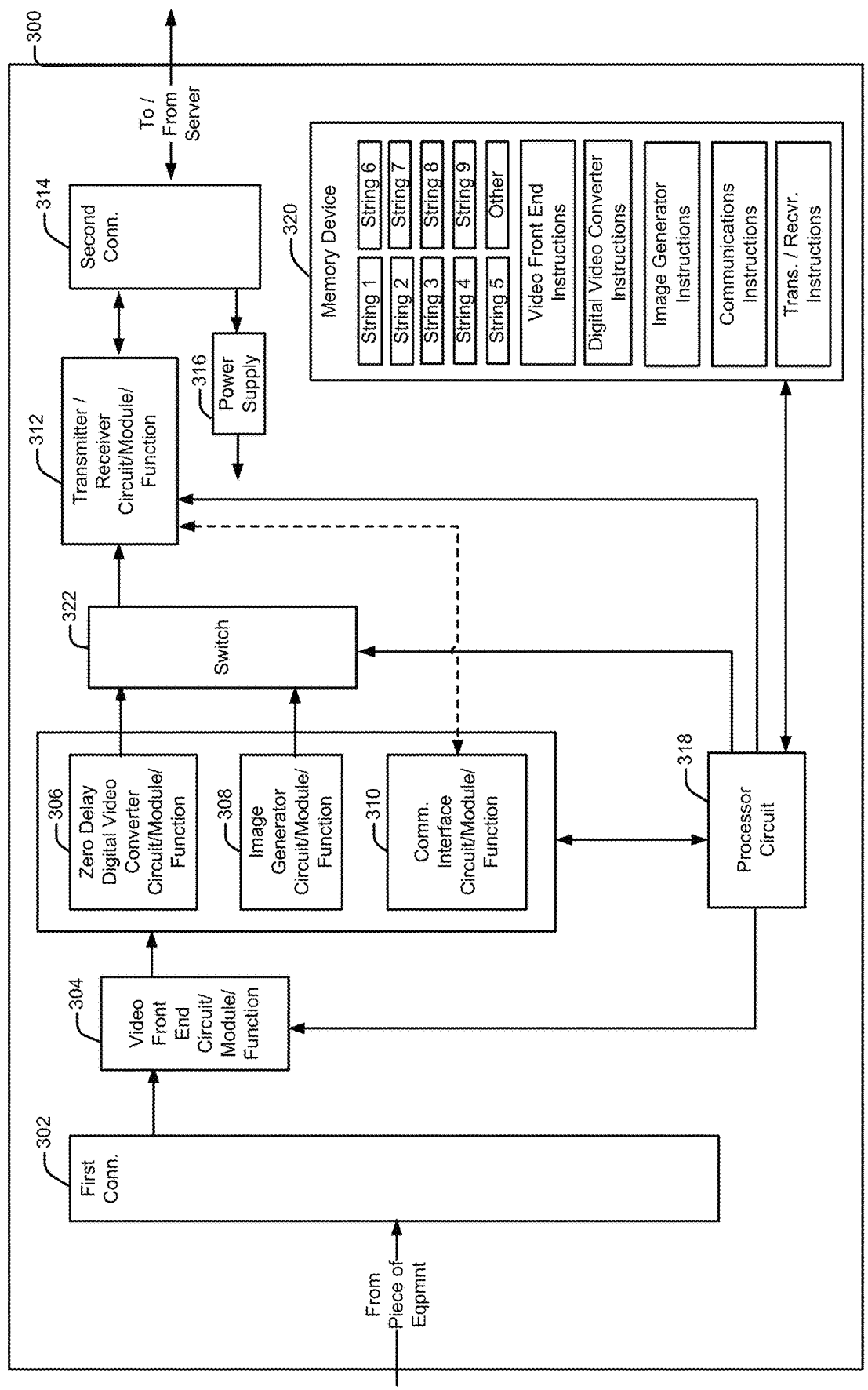
FIG. 3 is a block diagram of a converter device according to one aspect.

FIG. 3 is a block diagram of a converter device 300 according to one aspect. The converter device 300 may include, a first connector 302, a video front end circuit/module/function 304 (hereinafter video front end 304), a digital video converter circuit/module/function 306 (hereinafter digital video converter 306), an image generator circuit/module/function 308 (hereinafter image generator 308), a communication circuit/module/function 310, a transmitter/receiver circuit/module/function 312 (hereinafter transmitter/receiver 312), a second connector 314, a power supply 316, a processor 318, and a memory 320. This list is illustrative and not limiting.

The first connector 302 may be configured to couple to a plurality of input/output connector types, thereby accommodating the plurality of input/output connectors that may be expected to be serviced by the converter device 300. Input signal interface types may include any of a plurality input formats that may be expected to be serviced by the converter device 300. In one aspect, the interfaces may be those defined by national or international standards. Interfaces may include, for example, RGB analog, S-Video, or other types of analog inputs, any of a plurality of digital interfaces such as, for example, High-Definition Multimedia Interface (HDMI), Digital Visual Interface (DVI), Serial Digital Interface (SDI), and/or Universal Serial Bus (USB). The preceding list is illustrative and not limiting.

The video front end 304 may be a decoder, for example, configured to decode standard or high definition video signals. For example, video comes in a variety of formats. Some analog video formats come with the color information, brightness information, and video sync signals "encoded" into a single video feed. Other non-analog video formats such as DVI or serial digital interface (SDI), HD-SDI, 3G-SDI are digital formats that are encoded with extra information so that the receiving device can easily lock on to these signals and decode them. The video front end 304 could include an analog-to-digital converter for reception of analog signals and/or an equalizer for digital formatted signals. The video front end 304 may generally be configured to place any of a predetermined number of types of input signals into a digital video format.

The digital video converter 306 may convert the format of the digital data received from the video front end 304 to a second digital format guaranteed to be useable by a system processor (e.g., 124, FIG. 1) associated with a digital video matrix (e.g., 120, FIG. 1). For example, in one aspect the second digital format may be an RGB 4:4:4 digital format. The conversion may be done on a pixel-by-pixel timeframe. The format of the signal received by the digital video converter 306 may not be the same as the format of the digital signal output from the digital video converter 306. The digital video converter 306 may be a "zero delay" digital video converter. The term "zero delay" may infer that there is substantially little delay in the circuit. In one aspect, actual delay of a zero delay converter may be less than about 10 microseconds. In some aspects, the digital video converter 306 may clean up a synchronization signal. In some aspects, the output of the digital video converter 306 may be four high-speed serial lines in parallel.

The image generator 308 may be used to generate, in one aspect, a video signal representative of an informational image.

The communication circuit/module/function 310 may serve as a bidirectional communication interface between the digital video matrix (e.g., 120, FIG. 1) and the converter device 300.

Generating Informational Display and Message

Figure 4:
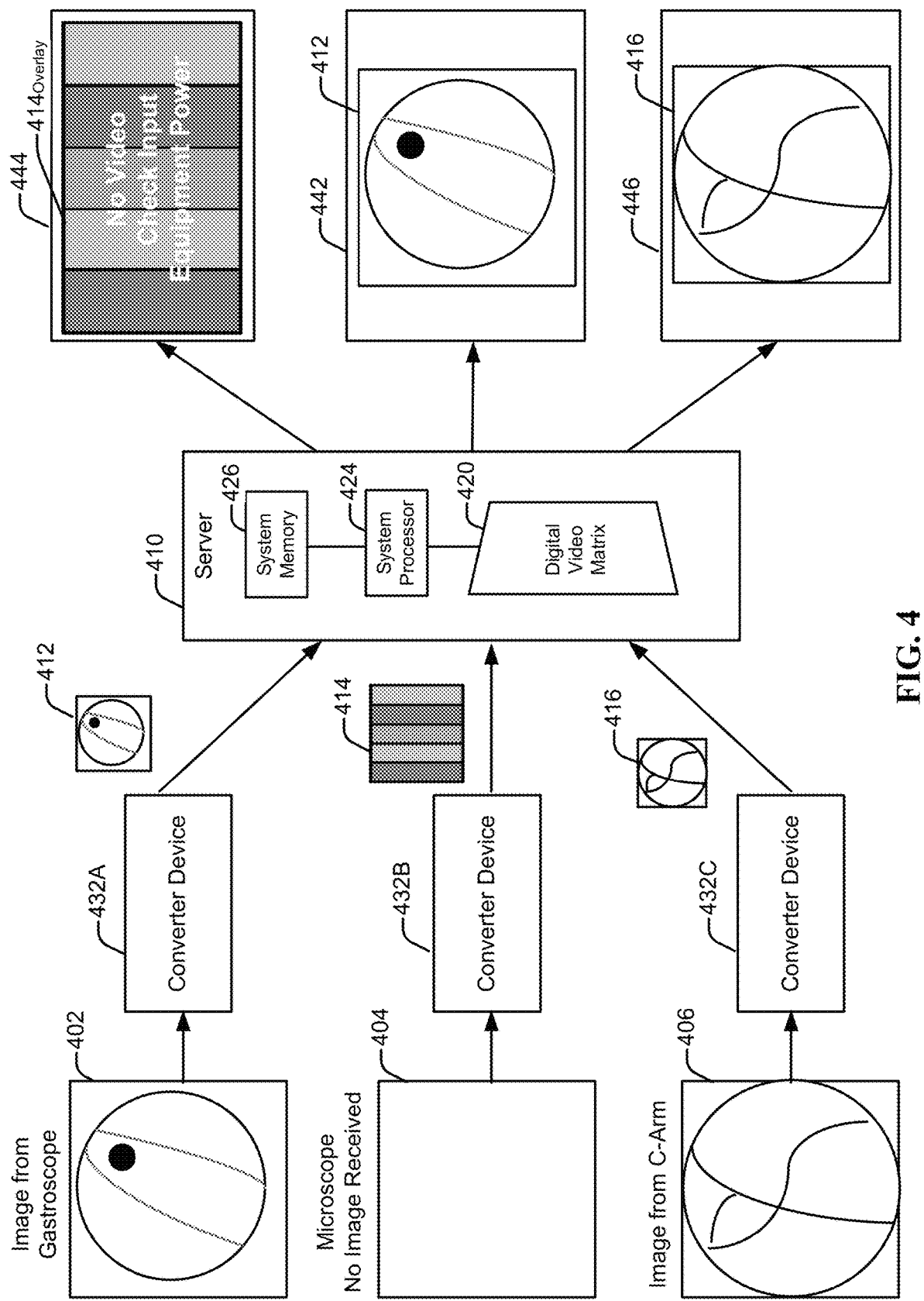
FIG. 4 illustrates an informational message, such as one that may be generated by an image generator of a converter device.

FIG. 4 illustrates an informational message, such as one that may be generated by an image generator (see, for example, circuit 308 of FIG. 3) of a converter device. As illustrated in FIG. 4, a system including a server 410 having a digital video matrix 420 (similar to 120, FIG. 1), a system processor 424 (similar to 124, FIG. 1), and a system memory 426 (similar to 126, FIG. 1) may receive input data from a number of converter devices 432A, 432B, and 432C (similar to 132, FIG. 1). The output of the server 410 may be routed to any or all of video monitors 442, 444, 446.

A converter device 432A may receive data representative of an image received from a gastroscope 402. The converter device 432A may convert the data from a first format to a second format for output to the server 410. The output data 412 of the converter device 432A may include data representative of the image received at the input of the converter device 432A. The output data 412 of the converter device 432A may be routed by the server 410 to a video monitor 442 for display thereon.

Another converter device 432C may receive data representative of an image received from a C-Arm 406. The converter device 432C may convert the data from a first format to a second format for output to the server 410. The output data 416 of the converter device 432C may include data representative of the image received at the input of the converter device 432C. The output data 416 of the converter device 432C may be routed by the server 410 to a video monitor 446 for display thereon.

Another converter device 432B may be coupled to a microscope, but no video signal 404 is being received from the microscope at the input of the converter device 432B. The image from the microscope may have been intended to be routed by the server 410 to a video monitor 444. The lack of a video signal 404 from the microscope may be due, for example, to the power for the microscope being in an OFF state. To indicate that the problem is not in the path from, for example, the output of the converter device 432B to the monitor 444, the converter device 432B may generate, using an image generator (see, for example, not shown, circuit 308 of FIG. 3) a predetermined image 414. The image 414 may be, for example, a fixed image, such as a series of vertical stripes of different colors abutted against one another. Other images, including moving images, may be used.

In one aspect, the system processor 424 may cause informational text to overlay (or equivalent thereof) the predetermined image 414. The resultant compound image 114Overlay may read, for example, "No Video. Check Input Equipment Power" and may include one or more items of identification of the piece of equipment to which the converter device 432B was pre-programmed to be coupled to. For example, the text overlay (or equivalent thereof) may read "No Video from Olympus model no. 12345 microscope, serial number 102030. Check microscope power." Other text overlays (or equivalents thereof) may be used. Notably, the predetermined image 414 and compound image 114Overlay automatically appears and may be displayed until the processor of the converter device 432 validates the incoming video signal. Therefore, in one aspect, it is the converter device 432 that automatically generates the predetermined image 414, determines if the input video signal or predetermined image 414 is presented to the server 410 (via a determination of the validity of the input video signal) and provides the data for the compound image 114Overlay.

Converter Device (Continued)

Returning now to FIG. 3, the transmitter/receiver 312 may be, in one aspect, an aggregator of data. For example, if the digital video converter 306 outputs a plurality of serial data streams, each data stream at a given speed, the transmitter/receiver 312 may take the plurality of signals and combine them into a single higher-speed video format output signal for transmission to the digital video matrix (e.g., 120, FIG. 1).

In another aspect, the transmitter/receiver 312 may receive instructions/queries from the system processor (e.g., 124, FIG. 1) associated with a digital video matrix (e.g., 120, FIG. 1) and forward the instructions/queries to the communication interface 310. The communication interface 310 may, in turn, forward the instructions/queries to the processor 318 of the converter device 300. The processor 318 may calculate, or otherwise obtain, a response to the instructions/queries and return the response to the communication interface 310. The communication interface 310 may, in turn, return the response to the transmitter/receiver 312. The transmitter/receiver 312 may, in turn, forward the response to the system processor (e.g., 124, FIG. 1) associated with a digital video matrix (e.g., 120, FIG. 1).

The second connector 314 may include contacts forming a physical interface that may be of a proprietary or non-proprietary configuration. In one aspect, the connector 314 may be configured to be coupled, directly or via an interface (such as interface 134, FIG. 1), to the server (e.g., 122, FIG. 1 or 222, FIG. 2).

The power supply 316 may include, in one aspect, an internal voltage converter (not shown) to convert a DC line voltage to one or more predetermined DC voltages for operating the converter device 300. In another aspect, the power supply 316 may receive operating voltage(s) from an interface (such as interface 134, FIG. 1) and distribute the received operating voltage(s) to the components of the converter device 300. In one aspect, the power supply 316 may filter the operating voltage received from the interface (such as interface 134, FIG. 1) prior to distributing the operating voltage(s) to the components of the converter device 300.

The processor circuit 318 may read data, such as instructions and predefined data string values, from the memory 320. In one aspect, the instructions may cause the processor circuit 318 to configure the video front end 304, for example, to receive an input of a predetermined format from the piece of equipment to which it is coupled. For instance, the video front end 304 may be coupled to a piece of equipment that is expected to present an analog signal of a given format to the video front end 304. The processor circuit 318 may therefore issue commands to cause the video front end 304 to be configured for an analog-to-digital conversion. By way of another example, the video front end 304 may be coupled to a piece of equipment that is expected to present a digital signal in a standard definition format to the video front end 304. The processor circuit 318 may therefore issue commands to cause the video front end 304 to be configured to convert the digital signal in the standard definition format to another format suitable for input to the digital converter 306. In some aspects, the configuration of the video front end 302 may be accomplished by having the processor circuit 318 write predefined data to registers associated with the video front end 304. These registers may be used to configure the video front end 304 to accept one of a plurality of different types of input. In some aspects, the input and output of the video front end may have the same format.

In one aspect, the instructions may cause the processor 318 to configure the digital video converter 306. In one aspect, the instructions may cause the processor 318 to configure the image generator 308. In one aspect, the instructions may cause the processor 318 to configure the communication interface 310. In one aspect, the instructions may cause the processor 318 to configure the transmitter/receiver 312. Configurations may be accomplished, for example, by programming registers associated with the given circuit/module/function 306, 308, 310, 312 or otherwise communicate with the given circuit/module/function 306, 308, 310, 312.

In one aspect, the instructions may cause the processor 318 to write data to, or read data from, the memory 320. For example, an external device may send a query to the converter device 300 to retrieve certain information stored in the memory 320 of converter device 300. The information may include equipment identification information and/or values of various flags, and/or status of a video input signal presented to the converter device 300.

In one aspect, the instructions may cause the processor 318 to calculate a cumulative runtime of the piece of equipment and to write the calculated runtime to the memory 320. Calculations may be performed continually or periodically. The cumulative runtime could be, for example, the number of hours the piece of equipment has been in an ON state. For example, the converter may have a real-time clock that updates the memory once a minute while the equipment is in the ON state. The run time may be written to two memory locations in a toggle format. For instance, a first write is written to location 1, a second write is written to location 2, a third write is written to location 1, so on and so forth. If power is abruptly removed during a memory write, the last known good memory write may be used once the converter device is powered back on. By way of another example, the number of hours that the piece of equipment has presented a video valid signal to an input of the converter device 300 may be measured. This may be implemented, for example, by the zero delay digital video converter circuit/module/function 306, which may perform real time video timing measurements that are passed on to the processor circuit 318 for validation, e.g., to determine if the video is valid or invalid.

Keeping track of the runtime of a given piece of equipment may be useful if the equipment fails, and the warranty is tied to the amount of time the equipment is in use. Alternatively, the runtime can be calculated by the system processor (e.g., 124, FIG. 1) associated with the system as a whole. The resulting data can be written to the memory 320 of the converter device 300 from the system processor associated with the system as a whole.

As indicated above, the processor 318 of the converter device 300 may communicate with a system processor (e.g., 124, FIG. 1) that may have overall control of the system as a whole. The system processor may be located with the video matrix in a server, or may be part of a computer, such as a Linux computer, associated with the system. A user interface (not shown) may be located at any video monitor, for example in the operating room and/or remote to the operating room. The user interface may permit a user to enter data that can be saved as one or more strings within the memory 320 of the converter device. The processor 318 of the converter device 300 may communicate with the system processor during, for example, an initial set-up of the converter device 300.

The memory 320 may be a non-volatile memory, such as a flash memory. The processor 318 may communicate with the memory 320. The memory 320 may be used to store data, for example, in text strings that are unique to a given piece of equipment coupled to the converter device 300. The memory 320 may store, for example, the following strings of data that may be presented to the memory 320 during set-up of the converter device 300.

String 1: generic name of piece of equipment (e.g., surgical robot, surgical-light camera, microscope, C-arm, endoscope, ultrasound, or room observation camera);

String 2: model number of piece of equipment;

String 3: serial number of piece of equipment;

String 4: hours of operation (e.g., cumulative run-time) of the piece of equipment;

String 5: data indicative of whether the given piece of equipment provides equipment information in the video stream presented to the converter device 300 (e.g., a "modality provided by source" flag);

String 6: data indicative of whether the given piece of equipment provides patient information in the video stream presented to the converter device 300 (e.g., a "patient information provided by source" flag); and/or String 7: Input video status.

String 8: Asset tracking ID may include an asset ID number for real-time location system (RTLS) or other types of tracking devices attached to equipment.

String 9: De-Identification x-y coordinates used to provide location information of patient information embedded in the video which could be used to mask this information while conferencing or streaming video to remote locations in order to protect the patient's confidentiality.

The preceding list of strings is illustrative and not intended to be limiting. Information, such as that associated with the exemplary recited seven strings, or any other information, can be stored in the memory 320 of the converter device.

In one aspect, as indicated above, the zero delay digital video converter circuit/module/function 306 may perform digital video processing on an input signal and may provide detailed video timing data to the processor 318. The processor 318 may then determine if the detailed timing data provided by zero delay digital video converter circuit/module/function 306 is valid. In this way, according to this aspect, the converter device may determine that the input signal is a valid video input signal. The converter device may automatically, by action of the processor 318 and without any input from the server, use switch 322 to switch the signal presented to the zero delay digital video converter circuit/module/function 306 between the signal from the video front end circuit/module/function 304 and the signal from the image generator circuit/module/function 308 based on the determination.

In one aspect, the system, may be recording all data flowing into (and/or out of) the digital video matrix (e.g., 120, FIG. 1). Recordings may be made, for example, using a recorder 118E, FIG. 1. The recording may include recording data associated with any or all of the strings of data described above. Such data may be recorded as metadata. The system may also include in the recording, for example as metadata, patient information including patient demographics obtained, for example, from a hospital database. The system may also include this information with image capture of still frames, streaming, and conferencing.

Inclusion of data such as, but not limited to, the data described above may be important, for example, to a surgeon reviewing the image captures or recordings of data obtained during a surgery. First, association of records with patient identification information is important to patient safety. For correct diagnosis or follow-up care, the surgeon must be sure that the image capture or recording he or she is reviewing belongs to the correct patient. Second, by way of example, if a surgeon notes an anomaly, or an indication of anything of importance, the surgeon can associate that anomaly or indication to, for example, the model number and serial number of a given piece of equipment and/or any other information saved in the strings stored in the converter device 300. This could be important, for example, to determine whether the patient's condition caused the anomaly or whether the given piece of equipment caused the anomaly.

Inclusion of data such as, but not limited to, the data described above may also be important, for example, in determining if a given piece of is still under warranty. Many pieces of medical equipment do not come with the runtime indicator and do not record their runtime; nevertheless, warranties on the medical equipment may be based on runtime. Thus, the tracking and storage of cumulative runtime may be beneficial, for example, in disputes involving warranty expiration.

In one aspect, a converter device 300 may be permanently associated with a given piece of equipment (e.g., 102-114, FIG. 1). That is, each converter device 300 may be dedicated to one piece of equipment. Therefore the data, including cumulative runtime, stored in the memory 320 of the converter device 300 is unique to that piece of equipment. This feature may aid a hospital in determining whether a failed piece of equipment is under warranty. Additionally, this feature may aid a hospital in monitoring the expiry dates of clinical equipment warranties.

One or more of the information types recited above, and/or other information, may be entered into the memory 320 of the converter device 300 and stored for future use. The information may be entered, for example, during setup of the converter device 300, when the converter device 300 is initially coupled to the piece of equipment. The memory 320 may also include instructions that when executed by the processor 318 cause the processor 318 to perform the methods of one or more aspects of the system or converter device 300 described herein.

Display of Equipment and Patient Information

Figure 5:
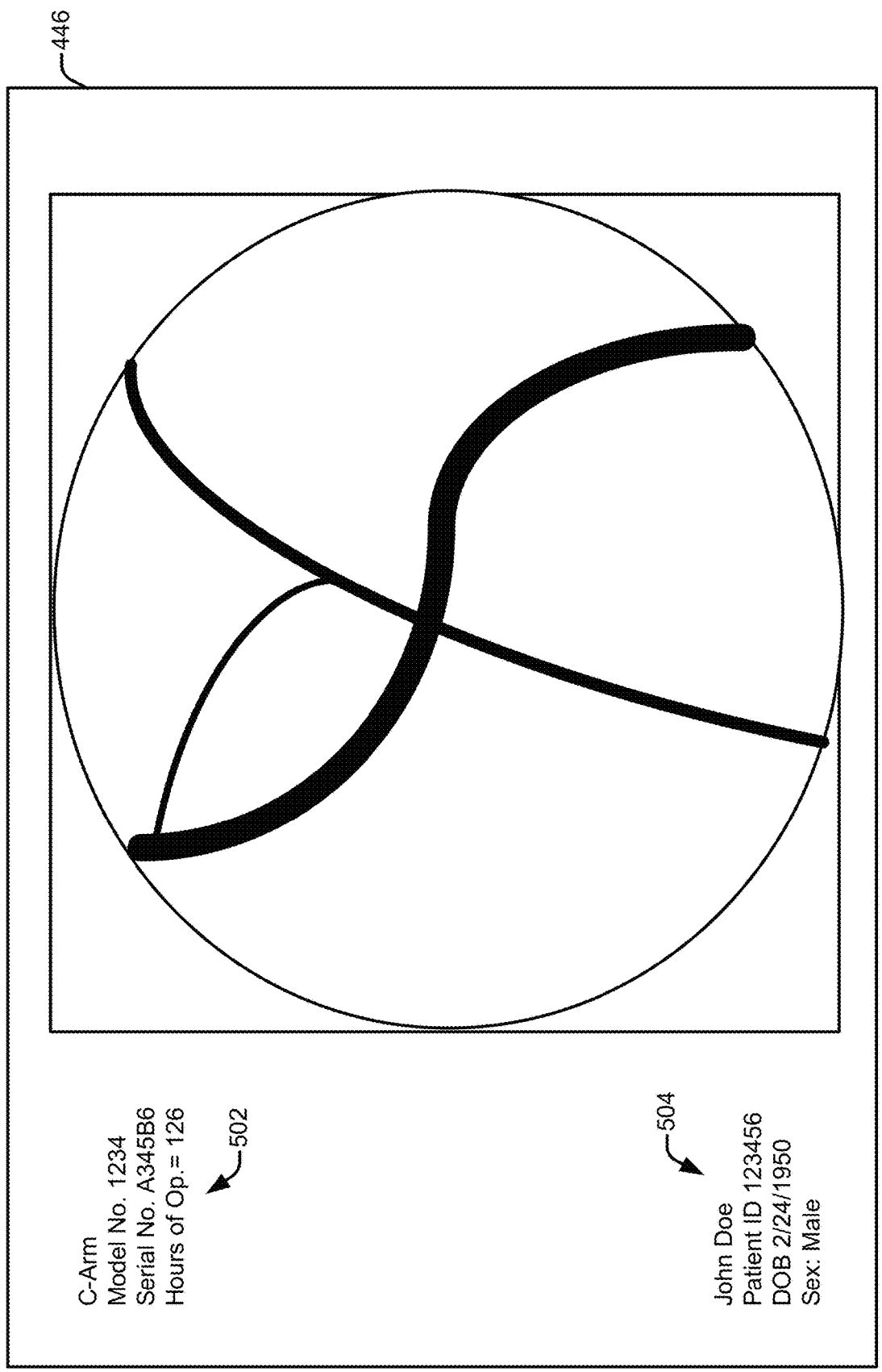
FIG. 5 is an illustration of a video monitor showing equipment information (e.g., modality) and patient information in the image field displayed by the video monitor.

FIG. 5 is an illustration of a video monitor 446 of FIG. 4 showing equipment information (e.g., modality) 502 and patient information 504 in an image displayed by a video monitor (e.g., video monitor 446). In one aspect, the equipment information 502 and/or patient information 504 may not obscure any of the patient video.

Figure 6A:
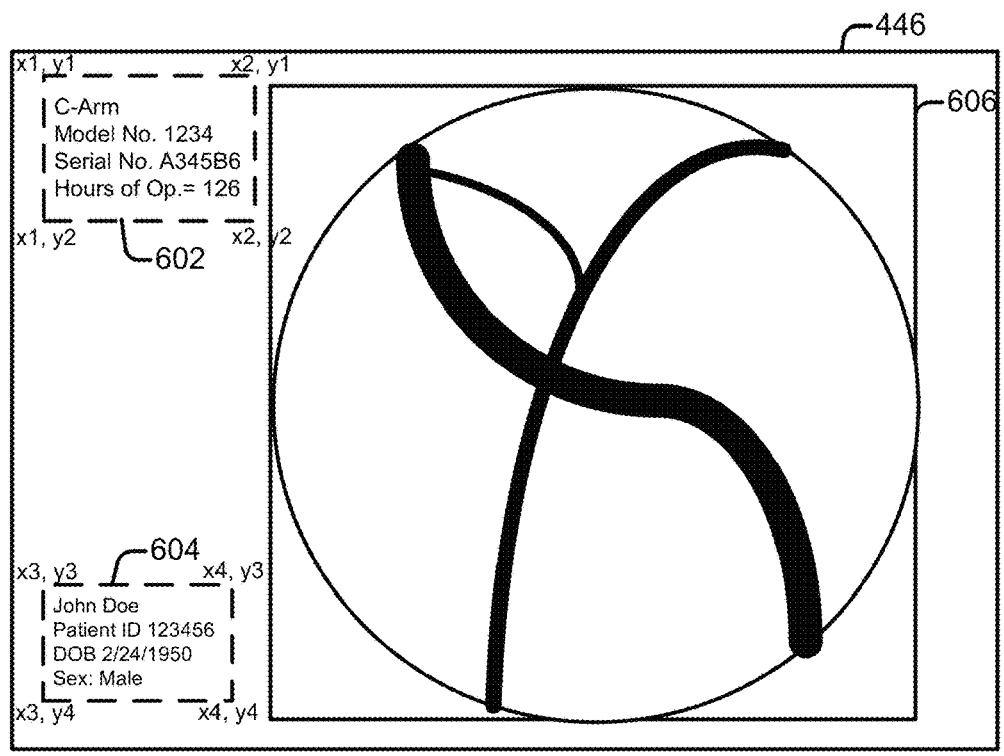
FIGS. 6A and 6B illustrate de-identification, where areas holding information may be masked.
Figure 6B:
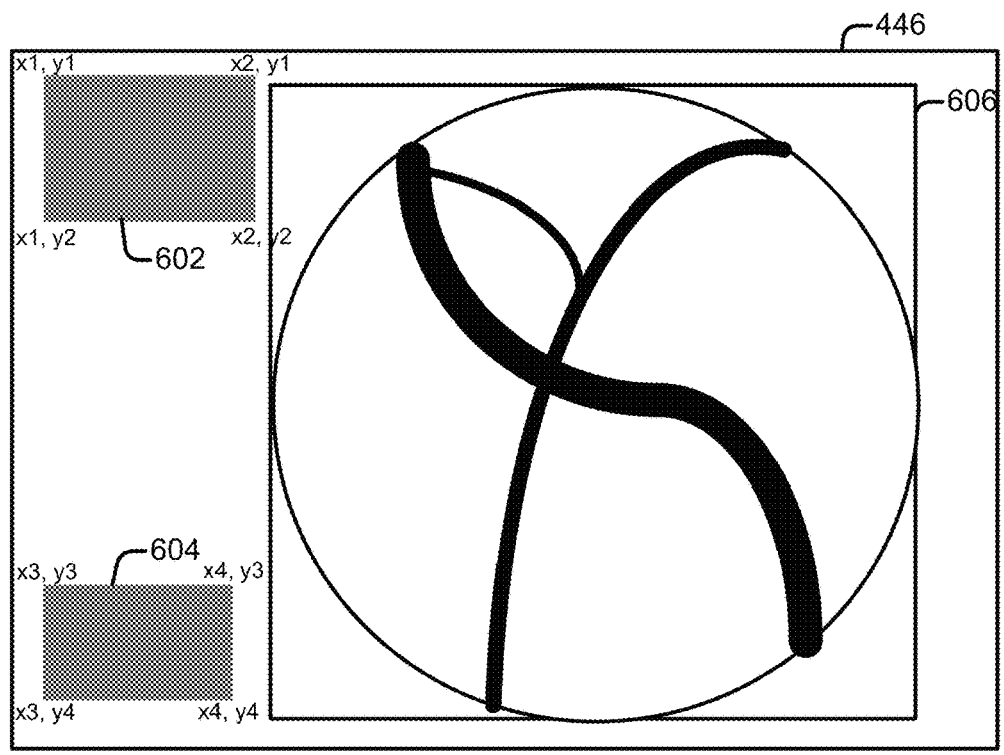

FIGS. 6A and 6B illustrate de-identification, where areas holding information may be masked. Masking as presented in FIG. 6B may protect patient confidentiality. In one aspect, de-identification coordinates may be created by the server and video matrix through a user interface after the converter device is coupled to a piece of equipment. The de-identification coordinates may then be stored in the memory of the converter device. The de-identification coordinates may define de-identification regions 602, 604 that are sized and positioned on the video image produced by a given piece of equipment such that the de-identification regions may be superimposed upon any or all information displayed on the video image, such as personal information. As shown in FIG. 6B, the de-identification regions 602, 604 may be used to mask the information from being visible on the image. De-identification coordinates may be read from the converter device and used to determine which portion(s) of the video the video matrix should mask out. This feature may find utility in scenarios whether patient information must be maintained in confidentiality, such as when the video is sent out to a streaming or conferencing codec. This feature advantageously stores the de-identification coordinates in one or more strings inside the memory of the converter device. In this way the information only needs to be established one time, when the converter is attached to a piece of equipment.

Set-Up and Use of Converter Device

Figure 7:
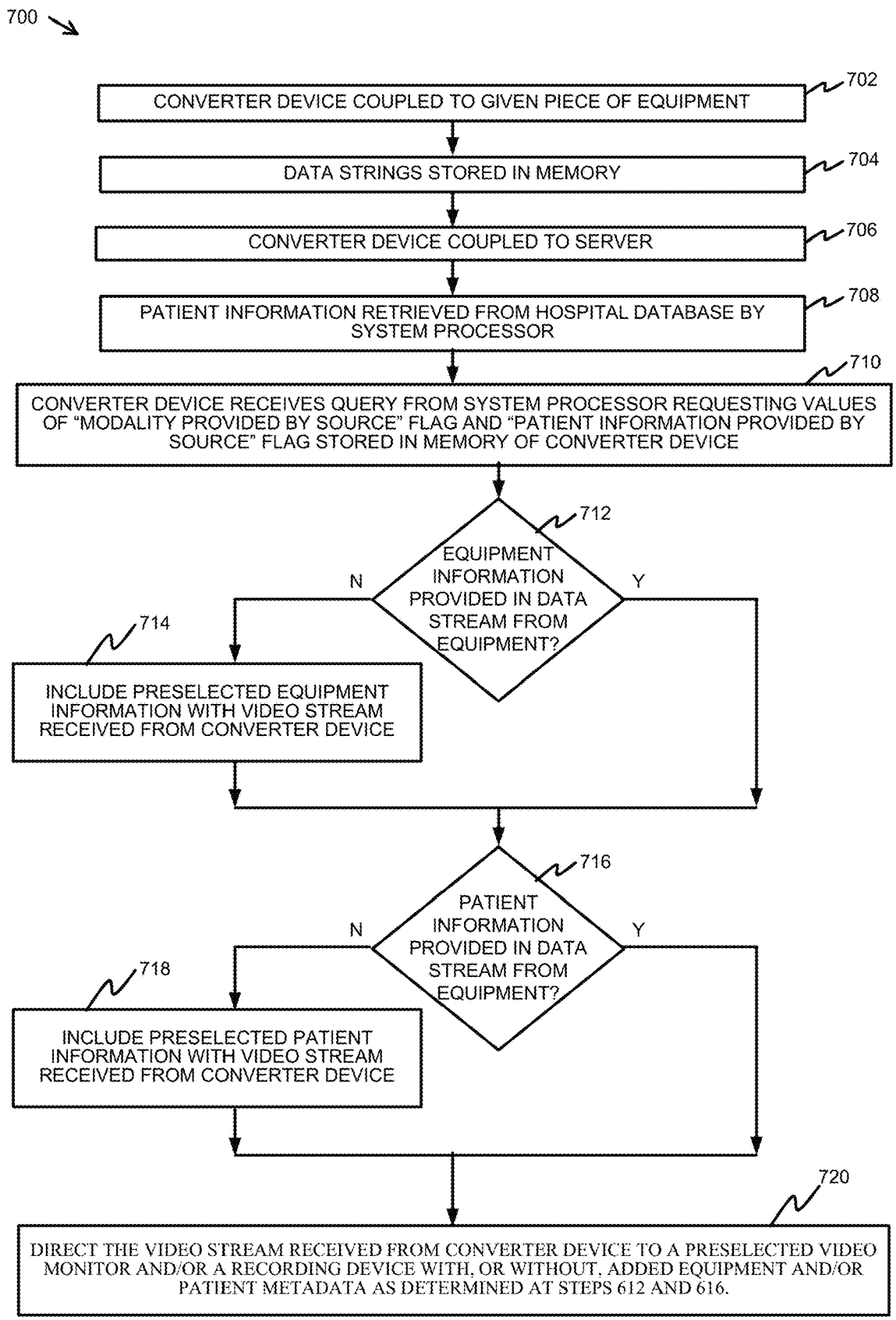
FIG. 7 is a block diagram illustrating a method of set-up and use of a converter device.

FIG. 7 is a block diagram illustrating a method 700 of set-up and use of a converter device. During set-up, the converter device may be coupled to a given piece of equipment 702. The converter device may be coupled to a source of power and to a communication network. The converter device may be recognized by the server. The server may be interchangeably referred to as the "server" and/or "video router/server" herein. According to some aspects, once recognized, a user can program or update any of the converter device's parameters from the server's user interface or from any remote connection over a network. According to some aspects, a user performing the set-up may input a set of data strings into a user interface. The data strings may be stored in memory 704. The set of strings may include, for example, String 1 and any or all of the remaining 8 strings (Strings 2-9) described above. During use the converter device may be coupled to a server of the system 706.

The system may obtain an identity of a patient, and may, using that identity, obtain patient information (demographics) from a hospital database via Health Level Seven (HL7) messaging 708. HL7 messaging is a standard used for electronic medical records, which manufacturers have agreed to use for communication between different systems. HL7 provides for messaging over a hospital's network. Information obtainable from a hospital's database may include patient name, patient initials, patient record identifier, patient demographics (e.g., age, race, sex, religion, address, etc.), as well as scheduling information indicating when the patient is scheduled for a given operating room and case type. Any or all of this information may be automatically pulled into the system from the hospital's network via HL7 messaging.

The system may query the converter device to determine if the piece of equipment coupled to the converter device provides information about the equipment and/or information about the patient to the converter device in the video feed from the piece of equipment 710.

If, at 712, the system, based on a response from the converter device, determines that a flag is set to indicate that the piece of equipment does not provide equipment information in its video stream to the converter device, then, at 714, the system includes, as metadata preselected equipment information with the video stream received from the converter device. If at 712 the system determines that the flag is set to indicate that the piece of equipment does provide equipment information in its video stream to the converter device, then the method proceeds to 716. If at 716 the system, based on the response from the converter device, determines that a flag is set to indicate that the piece of equipment does not provide patient information in its video stream to the converter device, then at 718 the system includes, as metadata, preselected patient information with the video stream received from the converter device. If at 716 the system determines that the flag is set to indicate that the piece of equipment does provide patient information in its video stream to the converter device, then the method proceeds to 720. At 720 the system directs the video stream received from the piece of equipment to a preselected video monitor and/or a recording device with, or without, added equipment and/or patient metadata as determined at steps 712 and 716.

According to one aspect, the system is one which, based on data stored in the converter device, may take data from one or more sources and associate that data with a video image provided by a piece of equipment, such as a clinical piece of equipment. The association may be by addition of the data to the video stream as metadata and/or as application of the data, in text overlay form (or equivalent thereof), within an image field of an image produced from the video stream. The application of the text to the image may be turned on or off, on any one or more video monitors, on any recording or image capture, streaming or conferencing, based on requirements of patient confidentiality. The application of the text to the image may be done in real time, or very near real time based, at least in part, on the delay of the video signal through the video converter device.

Figure 8:
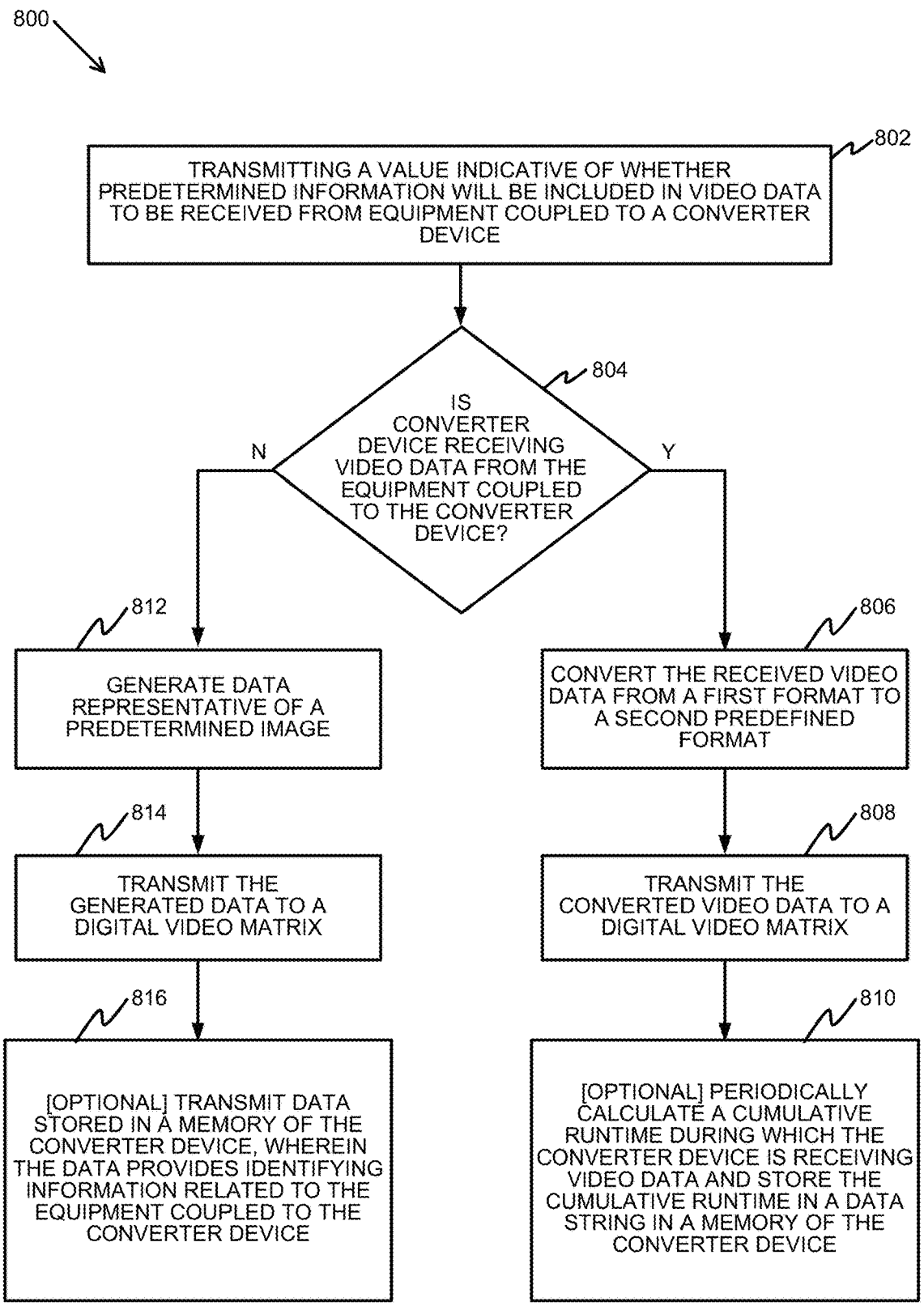
FIG. 8 is a block diagram illustrating a method 800 of use of a converter device.

FIG. 8 is a block diagram illustrating a method 800 of use of a converter device. The method may be operational at the converter device. A value indicative of whether predetermined information will be included in video data to be received from equipment coupled to the converter device may be transmitted from the converter device 802. A determination of whether the converter device is receiving video data from the equipment coupled to the converter device may be made 804. If the converter device is receiving video data, the received video data may be converted from a first format to a second predefined format at the converter device 806. The converted video data may be transmitted to a digital video matrix 808. As an optional step, a calculation of a cumulative runtime, during which the converter device is receiving video data, may be made and the result of the calculation of cumulative runtime may be stored in a data string in a memory of the converter device 810. The calculations may be performed periodically. If the converter device is not receiving video data, the converter device may generate data representative of a predetermined image 812. The converter device may then transmit the generated data to a digital video matrix 814. As an optional step, the converter device may transmit data stored in a memory of the converter device, wherein the data provides identifying information related to the equipment coupled to the converter device 816. The transmitted data may be used to add detailed text to (or over) the predetermined image.

According to one aspect, the converter device may provide a predetermined video pattern after being connected to a power supply or power supply and communications network. The converter device's parameters (e.g., the stored strings) may be read by the video matrix (e.g., 120, FIG. 1) and/or a processor (e.g., 124, FIG. 1) of a server (e.g., 122, FIG. 1) and then one or more of the converter device's parameters may be overlaid by the video matrix on top of the predetermined video pattern as an informative message for an end user. For example, an ultrasound machine's converter may be plugged into a power source and communication network. A predetermined video pattern may be generated and sent to the video matrix. The video matrix and/or server may read the converter device's parameters and overlay a message on top of the predetermined video pattern such as "Ultrasound—Please Power On Your Mobile Equipment." In one aspect, the signal applied to the input of the zero delay digital video converter circuit/module/function 306 may be from the output of a single pole double throw switch. The input to the switch may come from either the video front end circuit/module/function 304 or the image generator circuit/module/function 308, depending on the position of the switch. The processor circuit 318 may control the position of the switch.

One or more of the components and functions illustrated in the drawings may be rearranged and/or combined into a single component or embodied in several components without departing from the invention. Additional elements or components may also be added without departing from the invention. While certain exemplary embodiments have been described and shown in the accompanying drawings, it is to be understood that such embodiments are merely illustrative of and not restrictive of the present disclosure, and that the present disclosure should not be limited to the specific constructions and arrangements shown and described, since various other modifications are possible. Therefore, it is to be understood that, within the scope of the appended claims, embodiments of the present disclosure may be practiced other than as specifically described herein.

Specific implementations shown and described are only examples and should not be construed as the only way to implement the present disclosure unless specified otherwise herein. It is readily apparent to one of ordinary skill in the art that the various examples in the present disclosure may be practiced by numerous other partitioning solutions.

One or more of the components, acts, features, and/or functions described herein and illustrated in the drawings may be rearranged and/or combined into a single component, act, feature, or function or embodied in several components, acts, features, or functions. Additional elements, components, acts, and/or functions may also be added without departing from the invention. Algorithms described herein may also be efficiently implemented in software and/or embedded in hardware.

In the description, elements, module/circuit/functions, and functions may be shown in block diagram form in order not to obscure the present disclosure in unnecessary detail. Conversely, specific implementations shown and described are exemplary only and should not be construed as the only way to implement the present disclosure unless specified otherwise herein. Additionally, block definitions and partitioning of logic between various blocks is exemplary of a specific implementation. It is readily apparent to one of ordinary skill in the art that the present disclosure may be practiced by numerous other partitioning solutions. For the most part, details concerning timing considerations and the like have been omitted where such details are not necessary to obtain a complete understanding of the present disclosure and are within the abilities of persons of ordinary skill in the relevant art.

Also, it is noted that the embodiments may be described as a process that is depicted as a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a function, a procedure, a subroutine, a subprogram, etc. When a process corresponds to a function, its termination corresponds to a return of the function to the calling function or the main function.

Those of ordinary skill in the art would understand that information and signals may be represented using any of a variety of different technologies and techniques. For example, data, instructions, commands, information, signals, bits, symbols, and chips that may be referenced throughout this description may be represented by voltages, currents, electromagnetic waves, magnetic fields or particles, optical fields or particles, or any combination thereof. Some drawings may illustrate signals as a single signal for clarity of presentation and description. It will be understood by a person of ordinary skill in the art that the signal may represent a bus of signals, wherein the bus may have a variety of bit widths and the present disclosure may be implemented on any number of data signals, including a single data signal.

It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed there or that the first element must precede the second element in some manner. In addition, unless stated otherwise, a set of elements may comprise one or more elements.

Moreover, a memory, memory device, and/or storage medium may represent one or more devices for storing data, including read-only memory (ROM), random access memory (RAM), magnetic disk storage mediums, optical storage mediums, flash memory devices and/or other machine-readable mediums and, processor-readable mediums, and/or computer-readable mediums for storing information. The terms "machine-readable medium," "computer-readable medium," and/or "processor-readable medium" may include, but are not limited to non-transitory mediums such as portable or fixed storage devices, optical storage devices, and various other mediums capable of storing, containing, or carrying instruction(s) and/or data. Thus, the various methods described herein may be fully or partially implemented by instructions and/or data that may be stored in a "machine-readable medium," "computer-readable medium," and/or "processor-readable medium" and executed by one or more processors, machines and/or devices.

Furthermore, embodiments may be implemented by hardware, software, firmware, middleware, microcode, or any combination thereof. When implemented in software, firmware, middleware, or microcode, the program code or code segments to perform the necessary tasks may be stored in a machine-readable medium such as a storage medium or other storage(s). A processor may perform the necessary tasks. A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The various illustrative logical blocks, modules, module/circuit/functions, elements, and/or components described in connection with the examples disclosed herein may be implemented or performed with a general purpose processor, a digital signal processor (DSP), an application specific integrated circuit (ASIC), a field programmable gate array (FPGA) or other programmable logic component, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing components, e.g., a combination of a DSP and a microprocessor, a number of microprocessors, one or more microprocessors in conjunction with a DSP core, or any other such configuration. A general-purpose processor, configured for executing embodiments described herein, is considered a special purpose processor for carrying out such embodiments. Similarly, a general-purpose computer is considered a special purpose computer when configured for carrying out embodiments described herein.

The methods or algorithms described in connection with the examples disclosed herein may be embodied directly in hardware, in a software module executable by a processor, or in a combination of both, in the form of processing unit, programming instructions, or other directions, and may be contained in a single device or distributed across multiple devices. A software module may reside in RAM memory, flash memory, ROM memory, EPROM memory, EEPROM memory, registers, hard disk, a removable disk, a CD-ROM, or any other form of storage medium known in the art. A storage medium may be coupled to the processor such that the processor can read information from, and write information to, the storage medium. In the alternative, the storage medium may be integral to the processor.

Those of skill in the art would further appreciate that the various illustrative logical blocks, modules, module/circuit/functions, and algorithm steps described in connection with the embodiments disclosed herein may be implemented as electronic hardware, computer software, or combinations of both. To clearly illustrate this interchangeability of hardware and software, various illustrative components, blocks, modules, module/circuit/functions, and steps have been described above generally in terms of their functionality. Whether such functionality is implemented as hardware, software, or a combination thereof depends upon the particular application and design selections imposed on the overall system.

The various features and aspects described herein can be implemented in different systems without departing from the invention. It should be noted that the foregoing aspects are merely examples and are not to be construed as limiting the invention. The description of the various aspects is intended to be illustrative, and not to limit the scope of the claims. As such, the present teachings can be readily applied to other types of apparatuses and many alternatives, modifications, and variations will be apparent to those skilled in the art.

What is claimed is:

1. A system, comprising:
a plurality of converter devices, wherein each converter device is configured to serve a respective video source equipment,
each converter device comprising:
a first connector configured to communicatively couple to the video source equipment and receive video in a first format from the video source equipment,
a second connector configured to output the video in a second format,
a non-volatile memory circuit configured to store at least one flag value indicative of a presence of at least one of equipment information or patient information superimposed on the video received from the video source equipment, and
a processing circuit, communicatively coupled to the first connector, the second connector, and the non-volatile memory circuit, and configured to convert the video from the first format to the second format;
a matrix switch configured to communicatively couple to the second connector and further configured to communicatively couple to one or more video destination devices; and
a system processor configured to communicatively couple to the matrix switch and at least one of the plurality of converter devices, the system processor configured to:
transmit a query to the at least one of the plurality of converter devices requesting transmission of the at least one flag value stored at the non-volatile memory circuit, the at least one flag value indicative of the presence of at least one of the equipment information or patient information superimposed on the video received from the video source equipment, and the processing circuit of the at least one of the plurality of converter devices receiving the query is configured to transmit the at least one flag value to the system processor in response to receiving the query,
receive the at least one flag value from the at least one of the plurality of converter devices indicating that at least one of the equipment information or patient information is superimposed on the video received from the video source equipment, and
instruct the matrix switch to route the video in the second format from the second connector to at least one of the one or more video destination devices.

2. The system of claim 1, wherein the non-volatile memory circuit is further configured to store de-identification coordinates indicating spatial regions of the video that include at least one of the equipment information or patient information.

3. The system of claim 1, wherein the system processor is further configured to:
receive de-identification coordinates stored at the non-volatile memory circuit; and
utilize the de-identification coordinates to mask spatial regions that include at least one of the equipment information or patient information in the video.

4. The system of claim 1, wherein the system processor is further configured to:
receive a first video signal from a first converter device of the plurality of converter devices, the first video signal based on an original video signal provided by a first video source equipment communicatively coupled to the first converter device;
receive a first flag value from the first converter device;
generate a second video signal that includes at least one of a first equipment information or first patient information superimposed onto the first video signal when the first flag value indicates that at least one of the first equipment information or first patient information is not superimposed on the original video signal; and
instruct the matrix switch to route the second video signal to the at least one of the one or more video destination devices.

5. The system of claim 1, wherein the least one of the plurality of converter devices is removably coupled to the video source equipment and removably coupled to the matrix switch.

6. The system of claim 1, wherein at least one converter device of the plurality of converter devices includes an image generator circuit configured to provide a pre-defined video pattern, and the processing circuit of the at least one converter device is configured to:
output video in the second format to the matrix switch when the at least one converter device does receive the video from the video source equipment, and
output the pre-defined video pattern to the matrix switch when the at least one converter device does not receive the video from the video source equipment.

7. The system of claim 1, wherein each of the plurality of converter devices further includes a housing that contains, at least partially, the processing circuit and the non-volatile memory circuit, the housing separate and independent to the video source equipment and the matrix switch.

8. The system of claim 1, wherein the video source equipment is medical imaging equipment.

9. A system, comprising:
a plurality of converter devices, wherein each converter device is configured to serve a respective video source equipment,
each converter device comprising:
a first connector configured to communicatively couple to the video source equipment and receive video in a first format from the video source equipment,
a second connector configured to output the video in a second format,
a converter circuit communicatively coupled to the first connector and the second connector and configured to convert the video from the first format to the second format,
a non-volatile memory circuit configured to store at least one flag value indicative of a presence of at least one of equipment information or patient information superimposed on the video received from the video source equipment,
an image generator circuit configured to provide a pre-defined video pattern, and
a processing circuit, communicatively coupled to the first connector, the converter circuit, the second connector, the non-volatile memory circuit, and the image generator circuit, and configured to:
output converted video in the second format from the second connector when the converter circuit does receive the video from the video source equipment, and output the pre-defined video pattern from the second connector when the converter circuit does not receive the video from the video source equipment;

a matrix switch configured to communicatively couple to the second connector and further configured to communicatively couple to one or more video destination devices; and a system processor configured to communicatively couple to the matrix switch and at least one of the plurality of converter devices, the system processor configured to:

transmit a query to the at least one of the plurality of converter devices requesting transmission of the at least one flag value stored at the non-volatile memory circuit, the at least one flag value indicative of the presence of at least one of the equipment information or patient information superimposed on the video received from the video source equipment, and the processing circuit of the at least one of the plurality of converter devices receiving the query is configured to transmit the at least one flag value to the system processor in response to receiving the query, receive the at least one flag value from the at least one of the plurality of converter devices indicating that at least one of the equipment information or patient information is superimposed on the video received from the video source equipment, and instruct the matrix switch to route the video in the second format from the second connector to at least one of the one or more video destination devices.

10. The system of claim 9, wherein the non-volatile memory circuit is further configured to store de-identification coordinates indicating spatial regions of the video that include at least one of the equipment information or patient information.

11. The system of claim 9, wherein the system processor is further configured to:

receive de-identification coordinates stored at the non-volatile memory circuit; and utilize the de-identification coordinates to mask spatial regions that include at least one of the equipment information or patient information in the video.

12. The system of claim 9, wherein the system processor is further configured to:

receive a first video signal from a first converter device of the plurality of converter devices, the first video signal based on an original video signal provided by a first video source equipment communicatively coupled to the first converter device;

receive a first flag value from the first converter device;

generate a second video signal that includes at least one of a first equipment information or first patient information superimposed onto the first video signal when the first flag value indicates that at least one of the first equipment information or first patient information is not superimposed on the original video signal; and instruct the matrix switch to route the second video signal to the at least one of the one or more video destination devices.

13. The system of claim 9, wherein at least one of the plurality of converter devices is removably coupled to the video source equipment and removably coupled to the matrix switch.

14. The system of claim 9, wherein each of the plurality of converter devices further includes a housing that contains, at least partially, the processing circuit, the non-volatile memory circuit, the converter circuit, and the image generator circuit, the housing separate and independent to the video source equipment and the matrix switch.

15. The system of claim 9, wherein the video source equipment is medical imaging equipment.

16. A method, operational at a converter device configured to serve a respective video source equipment and convert video received from the video source equipment in a first format to a second format, comprising:

receiving, at the converter device, the video received from the video source equipment, the converter device comprising:

a first connector configured to communicatively couple to the video source equipment and receive the video in the first format, a second connector configured to output the video in a second format, a non-volatile memory circuit configured to store at least one flag value indicative of a presence of at least one of equipment information or patient information superimposed on the video received from the video source equipment, and a processing circuit, communicatively coupled to the first connector, the second connector, and the non-volatile memory circuit, the method further comprising:

converting, by the processing circuit, video from the first format to the second format when the converter device does receive the video from the video source equipment;

outputting, by the processing circuit, the converted video in the second format from the second connector to a matrix switch when the converter device does receive the video from the video source equipment, outputting, by the processing circuit, a pre-defined video pattern from the second connector to the matrix switch when the converter device does not receive the video from the video source equipment, receiving, by the processing circuit, a query requesting transmission of the at least one flag value stored at the non-volatile memory circuit, the at least one flag value indicative of the presence of at least one of the equipment information or patient information superimposed on the video received from the video source equipment, and transmitting, by the processing circuit, the at least one flag value to a system processor in response to receiving the query, wherein the system processor is configured to instruct the matrix switch to route the video in the second format from the second connector to at least one of one or more video destination devices.

17. The system of claim 1, wherein at least one converter device of the plurality of converter devices is attached to the video source equipment and is configured to be physically located by a real-time location system.

18. The system of claim 9, wherein at least one converter device of the plurality of converter devices is attached to the video source equipment and is configured to be physically located by a real-time location system.

19. The method of claim 16, further comprising:

storing, by the processing circuit, in the non-volatile memory circuit, de-identification coordinates indicating spatial regions of the video that include at least one of the equipment information or patient information.

20. The method of claim 16, further comprising:
storing, by the processing circuit, in the non-volatile memory circuit, the at least one flag value indicative of the presence of at least one of the equipment information or patient information superimposed on the video received from the video source equipment.

* * * * *